Nov. 17, 1959 H. A. MAAS ET AL Plant Pat. 1,880

LEUCOPHYLLUM PLANT

Filed March 31, 1959

WITNESS

Addison E Avery

INVENTORS

HERBERT A. MAAS

HERBERT L. MAAS by Rummler & Snow

ATTYS.

United States Patent Office

Plant Pat. 1,880
Patented Nov. 17, 1959

1,880

LEUCOPHYLLUM PLANT

Herbert A. Maas and Herbert L. Maas, Seabrook, Tex.; said Herbert A. Maas assignor to said Herbert L. Maas Application March 31, 1959, Serial No. 803,336

1 Claim. (Cl. 47—60)

Our present discovery concerns a new variety of Leucophyllum Texanum plant of the botanical classification *Leucophyllum frutescens* (Scrophulariaceae), commonly known as Purple Sage or Texas Silverleaf.

Our new discovery originated as a seedling of an unpatented variety of *Leucophyllum frutescens* Alba, both seed and pollen parents, and is the result of breeding efforts carried on by us since 1951 in our nurseries at Seabrook, Texas. We have asexually reproduced and propagated this new plant, in our nurseries at Seabrook, Texas, from cuttings grown with intermittent mist in sand.

Our new variety of Leucophyllum plant is believed to be a definite and commercially valuable improvement over the parent variety and is particularly distinguished from its parents by the compact form of its growth, its heavy dense foliage, and its white flowers which are considerably larger than the flowers of the parents. Our new variety is further distinguished from its parents by the fact that it blooms prolifically and continuously from April through October, thus blooming earlier than the parent variety, for a considerably longer duration, and with many more flowers.

These and other distinguishing characteristics of our new plant variety are illustrated in the accompanying drawings in which.

Figure 1:
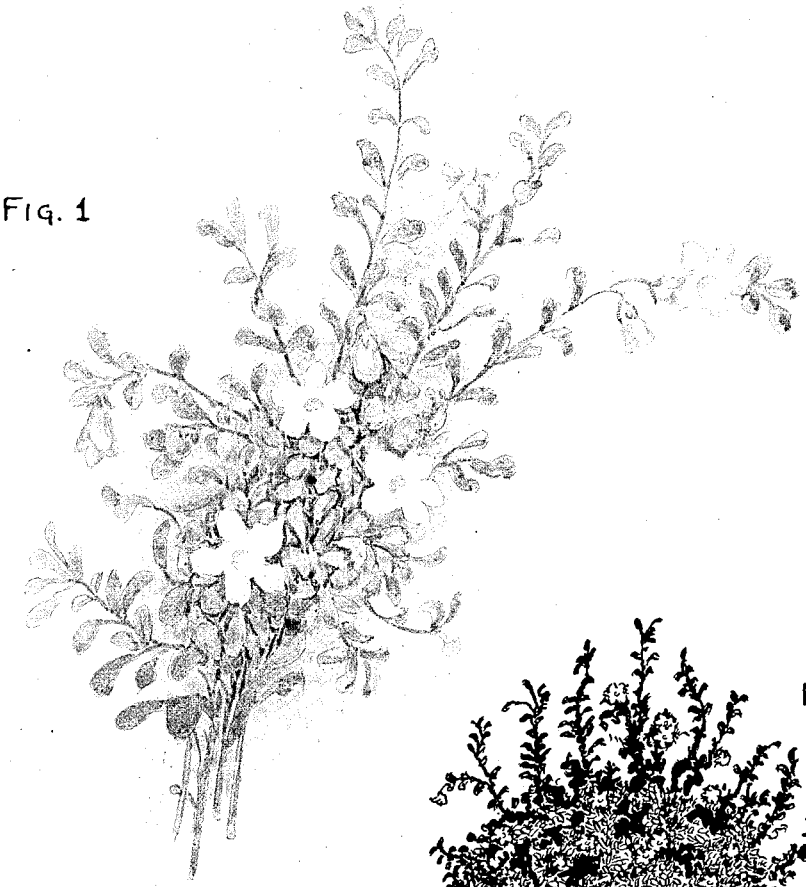
Figure 1 shows a spray of the foliage and flowers of the new variety in full color.
Figure 2:
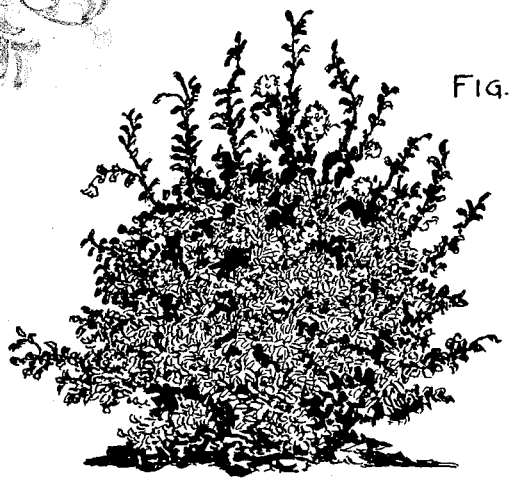
Fig. 2 is a pen and ink drawing showing the dense and compact form of growth of the new variety.
Figure 3:
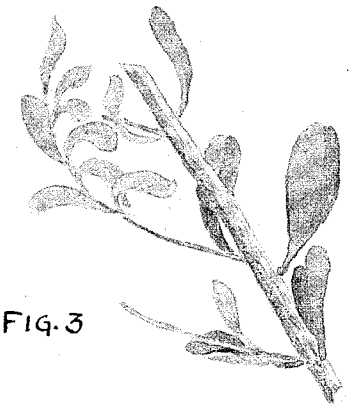
Fig. 3 is a fragmentary view in full color showing a portion of a branch and the manner in which the foliage grows thereon.
Figure 4:
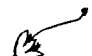
Fig. 4 is a pen and ink side elevation of a flower showing the elongate stock of the pistil.
Figure 5:
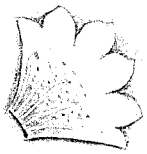
Fig. 5 is a view in color showing a split and spread open flower to illustrate the arrangement of the stamens and the yellow spotted inside wall of the throat or tube of the flower.

The following is a detailed description of our new variety of Leucophyllum plants, all references to color being in accordance with Maerz and Paul Dictionary of Color.

*Plant*

Growth: Vigorous, upright and dense. The plant grows from a 2½ inch pot liner to a 24 by 24 inch bush in one year, and ultimately reaches a height of about 8 feet. The plant is very hardy and withstands low temperatures to 10° F.

Wood: The trunk is smooth and stocky. The branches are smooth and are of a grey to green color. Angle of attachment of branches is 30 to 40 degrees. Lenticles number 24 per square inch and are 1/32 inch in diameter. There are no suckers.

Foliage: The foliage is heavy with a leaf size of 15/16 to 1 1/16 inches long, and 5/16 to 3/8 inch wide. The leaf shape is spaculate-retuse, the edges are smooth, and the texture is velvety. The leaf growth is sessile with occasional grey-green petioles of about 3/32 inch in length. There are no twigs.

Leaf coloring is as follows: Small leaves at tips of branches—top side, Plate 20, Letter B, No. 5; underside, silvery grey, Plate 18, Letter A, No. 3. Larger, older leaves—top side, Plate 22, Letter J, No. 7; underside, Plate 20, Letter B, No. 4.

*Flowers*

The flowers are hardy and bloom continuously from April through October. The flowers are axillary about 1 inch in diameter and the corolla is campanulate or funnel form with five to eight spreading lobes having obtuse tips. The flowers are solitary and pubescent and are white in color (Plate 9, Letter A, No. 1), with the exception that the inside surface of the tube contains many pale yellow spots, Plate 9, Letter K, No. 2.

The buds are hardy and about ½ inch in length with no pubescence and are pale green in color, Plate 18, Letter K, No. 2. The calyx is five parted and about ¼ inch insize. The anthers are tri-lobed and white in color with yellow pollen. The filaments are straight, about 3/8 inch long and are white in color. The pistil is single, straight and bi-carpel and is also white in color.

As grown in our nursery at Seabrook, Texas, our new variety of Leucophyllum plant has been observed to be fully resistant to all known pests or diseases prevalent in that area. It most resembles *Leucophyllum frutescens* Purpures, not patented, however, the new variety is particularly distinguished from *Leucophyllum frutescens* in that the latter has an obtuse form of leaf, while the new variety has a retuse leaf and its flowers are generally much larger. Other particular distinctions of the new variety are its more vigorous and compact growth habit, its smaller leaf, and its white flowers.

Having thus disclosed our new plant discovery we claim:

A new and distinct variety of Leucophyllum plant substantially as herein shown and described, characterized particularly by its more vigorous and compact habit of growth; its smaller retuse leaf; and its white flowers which bloom earlier, more prolifically, and for a longer duration.

No references cited.